United States Patent [19]

Ognier

[11] Patent Number: 5,800,381
[45] Date of Patent: Sep. 1, 1998

[54] MEDICAL GAS INSUFFLATOR WITH AUTOMATIC GAS FLOW CONTROL

[76] Inventor: Jean-François Ognier, Aulhac, 15240 Saignes, France

[21] Appl. No.: 537,892

[22] PCT Filed: Feb. 23, 1993

[86] PCT No.: PCT/FR95/00218

§ 371 Date: Oct. 30, 1995

§ 102(e) Date: Oct. 30, 1995

[87] PCT Pub. No.: WO95/23006

PCT Pub. Date: Aug. 31, 1995

[30] Foreign Application Priority Data

Feb. 25, 1994 [FR] France .................. 94 02483

[51] Int. Cl.[6] ............................................ A61M 37/00
[52] U.S. Cl. ................................ 604/26; 600/560
[58] Field of Search ................... 604/23, 26; 600/560

[56] References Cited

U.S. PATENT DOCUMENTS

| | | | |
|---|---|---|---|
| 3,982,533 | 9/1976 | Wiest | 604/26 |
| 4,048,992 | 9/1977 | Lindemann et al. | 604/26 |
| 4,207,887 | 6/1980 | Hiltebrandt et al. | 604/26 |
| 4,676,774 | 6/1987 | Semm et al. | 604/23 |
| 5,006,109 | 4/1991 | Douglas et al. | 604/26 |
| 5,328,458 | 7/1994 | Sekino et al. | 604/26 |
| 5,360,396 | 11/1994 | Chan | 604/23 |
| 5,439,441 | 8/1995 | Grimsley et al. | 604/26 |

FOREIGN PATENT DOCUMENTS 0 569 241 A3  11/1993  European Pat. Off.

*Primary Examiner*—Mark Bockelman
*Attorney, Agent, or Firm*—Herbert Dubno

[57] ABSTRACT

A medical insufflator has a flexible tube having a downstream end provided with a needle and an upstream end, the tube and needle forming an insufflation flow path for a neutral gas into a surgical cavity into which the needle is inserted, a supply of the neutral gas under pressure connected to the upstream end, and a flow-control valve along the flow path at the upstream end. It is operated by measuring an insufflation pressure at the upstream end of the insufflation path, continuously calculating intracavity pressure from the insufflation pressure by evaluating loss of pressure of the flow path, comparing the calculated intracavity pressure and a preset value of this intracavity pressure, and controlling the flow-control valve as a function of the result of the comparison with the above-mentioned preset value in order to continuously supply a flow of the neutral gas that is minimally sufficient to compensate for leakage of gas from the surgical cavity and to maintain the intracavity pressure generally equal to the preset value.

8 Claims, 6 Drawing Sheets

MEDICAL GAS INSUFFLATOR WITH AUTOMATIC GAS FLOW CONTROL

CROSS REFERENCE TO RELATED APPLICATIONS

This application is the U.S. national phase of PCT application PCT/FR95/00218 filed 23 Feb. 1995 with a claim to the priority of French 94 02483 itself filed 25 Feb. 1994.

The present invention relates to a medical gas insufflator with automatic gas-flow control used for diagnostic and surgical endoscopy to create by insufflation with a neutral gas an observation cavity and/or surgical space inside a human or animal body.

BACKGROUND OF THE INVENTION

The evolution of diagnostic endoscopy into surgical endoscopy has created new problems that need to be solved by the devices and instruments that are used. Medical insufflators belong to this category of supplies.

Originally conceived for dilating the cavity where the observation will take place and then, more recently, to create an "aseptic operating space," their characteristics have had to be adapted to the therapeutic means used by endoscopic surgeons, means which are naturally opposite to their good functioning (aspirators, vaporizers, fiber-cooling gases, laser-beam guides, neutral-gas electro-surgical devices, etc.) or that demand larger output in order to ventilate the surgical cavity (venting fumes from electro-surgery or lasers . . . )

Because of surgical demand this evolution has always resulted in an increase in the instantaneous gas flows and as a result insufflation pressures that currently reach values of 10,500 to 13,000 Pa (80 to 100 mm Hg) and even more. As a result the devices currently available on the market have safety-shutoff levels (fixed thresholds limiting the insufflation pressure) that are no longer compatible with the conditions required for the safety of the patients. These devices are all of the "pressure-regulating" type. Normally, in order to compensate for minor leaks, they have insufflation cycles that are very short with insufflation gas flows and pressures that are maximized.

Observation shows that during almost 90% of the time in an operation the effective gas flow is less than 3 l/min while under extreme conditions the instantaneous gas flow can reach 12 to 15 l/min.

In general the parameters to be sought or respected are the following:

- maintain an intracavity pressure between 0 and 3300 Pa (0 and 25 mm Hg);
- limit the insufflation pressure at the distal end of the insufflation or Veress needle to at most a safety threshold (to the best knowledge of applicant there has never been any clinical experimentation to determine this parameter; it seems nonetheless indispensable to remain below the local arterial pressure of 10,500 to 13,000 Pa, that is 80 to 120 mm Hg);
- only use a single connecting tube and a single transperitoneal device (needle or trocar) to input the gas, measure the intracavity pressure, evacuate fumes, or relieve intracavity over pressures;
- reach or exceed instantaneous gas flows of the insufflated gas of 12 liter/minute.

Different automatic gas insufflation devices which measure the insufflation pressure and the intracavity pressure have already been envisaged. The proposed systems generally combine a measuring device, means for holding the insufflated gas including one or more intermediate reservoirs, and an automatic regulation of the gas flow.

French 2,303,512 (Wiest) or its U.S. equivalent 3,982,533 describe a device for introducing into an abdominal cavity a limited quantity of carbonic gas, $CO_2$, under pressure contained in a reservoir, using a monitoring system controlling the insufflation and measuring the insufflation pressure, and a system for measuring the static or intracavity pressure. The device requires two Veress needles for insufflation or one dual-passage Veress needle.

German 2,544,467 (Richard wolf GmbH) describes a device for introducing into an abdominal cavity carbonic gas, $CO_2$, contained in a reservoir under pressure and using an expander, an insufflation conduit controlled by an Electrical valve, and a measuring conduit controlling the opening of this electrical valve. This devices requires two Veress needles for insufflation or one dual-passage Veress needle.

German 2,803,646 (Kurt Semm) relates to a device for introducing into the abdominal cavity carbonic gas, $CO_2$, using a multistage assembly comprising several intermediate expanders and reservoirs, characterized by a system using multiple paths for monitoring the flow. As realized this device is associated with other features described in the following documents.

Thus German 3,000,218 (Kurt Semm) has for object a system for statically measuring and controlling the intracavity pressure while using a single needle and a single tube based on a dual-period function cycle, that is an insufflation period during which the device measures the insufflation pressure (dynamic pressure) and a rest period during which the device measures the intracavity pressure (static pressure).

Similarly German 3,413,631 (Kurt Semm) describes an apparatus for calculating the intracavity pressure from the flow speed, the resistance to flow, and the insufflation pressure.

In current practice surgical teams have opted for devices needing only one insufflation conduit (connecting tube and Veress needle) assuring alternatively the measurement of intracavitary and insufflation pressures and thus rendering obsolete the two-conduit systems. The principal disadvantage of these means known to date lies in the impossibility of monitoring the intracavity pressure during the insufflation phase and with it the impossibility of reacting to any modification of the parameters in the operatic cavity (accidental overpressure, major leak, arousal of patient . . . )

Two other defects are generally ascribed to the marketed insufflators:

- they do not have a discharge device in case of intracavity overpressure;
- the injection of cold gas causes metabolic problems that are aggravated by the anesthesia.

OBJECTS OF THE INVENTION

The present invention has the object of avoiding these disadvantages and to this end it has the object of providing an insufflator that allows one to

- create and maintain a reference intracavity pressure, called "preset pressure," by regulating the insufflation gas flow while compensating strictly for leaks from the surgical cavity;
- determine the intracavity pressure from the insufflation pressure and from an evaluation of the loss of pressure;
- effecting a nonpolluting discharge in the event of an intracavity overpressure;

modulating the maximum insufflation pressure (safety threshold) as a function of the instantaneous flow;

heating the insufflated gas to body temperature.

SUMMARY OF THE INVENTION

At the base of the invention there is the verification (permitted by today's high-precision metering means such as electronic sensors and oscilloscopes) that for a given gas flow the difference between on the one hand the insufflation pressure Pi measured at the upstream end of the insufflation flow path where it joins the connecting tube running to the Veress needle and on the other hand the intracavity pressure Pa, is constant. This difference, which varies according to the gas flow and the configuration of the insufflation flow path, corresponds to the loss of pressure of the flow path hereinafter called $\Delta p$.

At rest this loss of pressure is zero and the pressure Pi measured at the upstream end of the insufflation flow path is equal to the intracavity pressure Pa.

As insufflation starts the pressure Pi measured at the upstream end of the flow path goes very rapidly from the level of the intracavity pressure to that of the insufflation pressure as illustrated by the curve showing the variation of the insufflation pressure according to FIG. 1 of the attached drawing. Experiments done by the applicant show that this temporary phase (between point t0 and point t0+$\Delta t$) lasts from 80 to 100 milliseconds.

During this temporary phase and taking into account its shortness, the variation of the intracavity pressure is insignificant. One can deduce from this that the loss of charge $\Delta p(t0)$ of the flow path at the instant to and for the flow D(t0) is equal to the variation of the insufflation pressure P1 during this temporary phase.

During the entire insufflation cycle one can follow the progression of the intracavity pressure by doing the following calculation:

$$P \text{ intracavity} = P \text{ insufflation} - \Delta p,$$

the different phases of the cycle being able to be described as follows:

from 0 to t0: The insufflator is at rest. The intracavity pressure decreases as a result of leaks or absorption by the body.

from t0 to t0+$\Delta t$: The apparatus insufflates gas at a constant flow rate. The pressure measured at the upstream end of the flow path increases very rapidly until it stabilized at p0+$\Delta p$ (after 80 to 100 milliseconds for the pressures and the flow paths used in medical devices). This pressure differential $\Delta p$ corresponds to the loss of pressure of the flow path for the flow rate and the configuration of the flow path at time t0. This loss of pressure can be recorded for the duration of the insufflation cycle in order to follow the progression of the intracavity pressure.

from t0+$\Delta t$ to t1: The apparatus insufflates gas at a constant rate. The difference between the intracavity pressure and the insufflation pressure remains constant and equal to $\Delta p$.

from t1 to t1+$\Delta t1$: The insufflation is interrupted. The measured pressure P1 drops very rapidly to reach the static or intracavity pressure.

from t1+$\Delta t1$ to t2: The apparatus is at rest. The measured pressure Pi corresponds to the intracavity pressure.

In applying this process the invention essentially has as object a medical insufflator with automatic control of the gas flow comprising an insufflation flow path for a neutral gas into a surgical cavity coupled with a supply of the neutral gas under pressure and a pilot flow-control valve along the flow path, the insufflator being characterized in that it comprises means for measuring an insufflation pressure at the upstream end of the insufflation path, means for continuously calculating the intracavity pressure from the insufflation pressure through the intermediary of an evaluation of the loss of pressure of the flow path, means for comparing the calculated intracavity pressure and a preset value of this intracavity pressure, and means for controlling the flow-control valve as a function of the result of the comparison with the above-mentioned preset value in order to continuously supply a flow of the neutral gas that is minimally sufficient to compensate for leakage of gas from the surgical cavity.

This produces a device which continuously calculates an intracavity pressure which is very close to the actual intracavity pressure (less than 2% deviation) and which by using a flow-control valve, in particular a proportional valve whose opening is controlled electronically, maintains the intracavity pressure at the preset level while reducing gas flow and insufflation pressures to the strict minimum while compensating accurately for gas leaks which cause a reduction of the maximum insufflation pressure to a level compatible with the safety of the patients. If there are large gas leaks the apparatus compensates instantaneously for these losses by changing the gas-flow rate and the maximum insufflation pressure (safety threshold). In addition the proposed device adapts itself instantaneously to all possible configurations of the flow path (tubes, insufflation needles or trocars, ...) and to any modifications of use conditions (bent or pinched tubing, ...)

More particularly the medical insufflator according to the invention is conceived to operate cyclically, the phases of insufflation and measurement being controlled by a clock, electronic means being provided for successively with each cycle:

measuring the intracavity pressure P0 at a starting instant to prior to insufflation which is equal to the static pressure at the upstream end of the insufflation flow path, displaying the intracavity pressure P0, starting the insufflation at the instant t0 with a flow that stays constant during the current cycle, measuring the insufflation pressure Pi at an instant t0+$\Delta t$, the duration $\Delta t$ being predetermined, calculating the loss $\Delta p$ of pressure of the flow path, evaluated as the difference Pi–P0 between the two earlier-measured pressures, recording to memory the loss $\Delta p$ of pressure specific to the current cycle, measuring the dynamic insufflation pressure Pi at an instant t after the instant t0+$\Delta t$, measuring the intracavity pressure Pa at the instant t equal to the difference Pi–$\Delta p$, displaying the intracavity pressure Pa thus determined and comparing it with the preset level.

According to another aspect of the invention the insufflator has a pneumatic control assembly which is comprised going from upstream to downstream of:

primary expansion means reducing to a low accurate pressure the pressure of the gas to be insufflated at the output of a supply of gas such as a bottle holding liquefied gas, a filter, an input safety valve, a secondary expansion capillary creating laminar flow and to which is associated a differential pressure sensor that determines the instantaneous gas flow, a proportional flow-control valve that is opened electrically in accordance with the instantaneous flow and the preset flow, an output safety valve, and a gas outlet associated with measuring means for the insufflation pressure used for calculating and controlling the intracavity pressure.

The thus constituted pneumatic control assembly has the advantage of being very compact. It also facilitates an instantaneous determination of flow rate by measuring the loss of pressure between the two extremities of the capillary thanks to a differential pressure sensor as described below. In any case this apparatus which effects an adiabatic expansion of the gas causes, if it is not corrected, a significant cooling of the gas especially at high flow rates and the insufflation of too cold gas can cause in the patent problems that are not negligible, even more so since during anesthesia body temperature is not correctly regulated. In addition the gas-flow measurement being determined by measuring the loss of pressure between the two ends of the capillary makes it necessary to maintain same at a constant temperature in order to get an accurate measurement. For this reason the pneumatic control assembly is advantageously provided with means for maintaining the temperature of the assembly and its parts, in particular ensuring reheating of the gas flowing through the capillary to a temperature about that of the body, that is in practice a temperature between 35° C. and 40° C.

According to a particular embodiment of the invention the subassembly including the expanding capillary and the differential pressure sensor is formed from two coaxial cylindrical element, one mounted in the other, the capillary being formed by an annular-section space between the two cylindrical elements while the two pressure taps are in the outside cylindrical element, respectively upstream and downstream from the region forming the capillary and serve to supply the differential pressure sensor that determines the instantaneous gas flow. The input safety valve is incorporated in the above-mentioned subassembly forming the expansion capillary, in particular at the center of the inside cylindrical element.

Such a setup is particularly advantageous for creating a gaseous expansion while determining the gas-flow rate and applying the known rules according to which the flow of gas in a conduit of constant section causes a regular pressure drop that is proportional to the length of the conduit and to the square of the speed of the gas. At a constant temperature and under "laminar" flow conditions (Reynolds number less than 2000) one can establish the relationship:

$$P2-P1=(\Lambda \times l \times \rho V m^2)/(h \times 2)$$

where:

P1=pressure "upstream"

P2=pressure "downstream"

l=length of the conduit:

$\Lambda$=coefficient of volumetric loss of pressure per unit of length h=distance between the two walls of the conduit $\rho$=volume mass of the gas at temperature T°

Vm=average flow speed.

Knowing that the gas flow D is expressed as D=S×Vm, where S is the flow cross section of the conduit, one can deduce $$D=\{<(P2-P1)\times 2S\times h>/\Lambda\rho\}^{1/2}$$

In the case of an annular-section conduit delimited by two cylindrical walls of respective diameters $\Phi 1$ and $\Phi 2$, the flow D is given by the following formula:

$$D=\{(\pi/2\Lambda\rho)\times(P2-P1)\times(\Phi 2^2-\Phi 1^2)\times(\Phi 2-\Phi 1)\}^{1/2}$$

As indicated above, the insufflation flow rate remains constant during each cycle. Nonetheless this flow increases from one cycle to the next in order to provide successive steps (progressive opening or closing of the flow-control valve) to compensate strictly for gas leaks in order to maintain or attain the preset intracavity pressure.

The ability of the device to compensate for leaks from the surgical cavity is effected by the variation of the function $$\delta=\delta(P_{preset}-P_{intracavity})/\delta t,$$

the derivative of the function $\Delta P=(P_{preset}-P_{intracavity})$

The parameters of the flow should respond to the following criteria:

As the offset $\Delta P$ between, the preset pressure and the intracavity pressure grows, the increase in flow between two cycles also grows in order rapidly to attain the preset pressure.

The increases in flow rate will be negative if the insufflation flow is greater than the leaks, that is if $\delta$ is negative; they will be positive if $\delta$ is positive.

The flow rate will be slightly superior to the escape of gas confirmed during steady-state operation.

It should not exceed the maximum insufflation pressure (see above).

The flow rate should be if necessary limited to the maximum preset flow (for example 11 l/min at the start of the operation), hereinafter called $D_{preset}$.

In what follows the parameters of the flow are given with reference to an example with reference to FIGS. 2 and 3 of the attached drawing, $\Delta D$ designating an increase in flow between the flow rate D1 of the first cycle and the fLow rate D2 of the second cycle immediately following the first one.

FIG. 2 illustrates the parameters as a function of the offset $\Delta P$ between the preset pressure and the static or intracavity pressure (expressed in mm Hg), the corresponding increase $\Delta D'$ of flow being expressed in l/min. Thus one has:

$$\Delta D'=(D2-D1)=0.3(P_{preset}-P_{intracavity})-0.6$$

$$\Delta D'=(D2-D1)=0.3(P_{preset}-P1)-0.6$$

FIG. 3 illustrates the parameters as a function of the offset $\delta(P_{preset}-P_{intracavity})$ expressing the ability to compensate for leaks even in the same system of units. The corresponding increase $\Delta D'$ in flow is thus given by:

$$\Delta D''=(D2-D1)=1.25\times\delta(P_{preset}-P_{intracavity})+0.5$$

$$\Delta D''=(D2-D1)=1.25\times(P_{preset}-P1-P_{intracavity})+0.5$$

$$\Delta D''=(D2-D1)=1.25\times\delta(P0-P1)+0.5$$

The flow rate D2 is determined based on the flow D1 and the elementary increases D' and D" according to the general relationship:

$$D2=S1+\alpha(\Delta D'+\Delta D'')$$

while respecting the condition:

$$0.1 \text{ l/min} < D2 < D_{preset}$$

Setting α=1 and taking into account the preceding relationships:

$$\Delta D' = 0.3(P_{preset} - P1) - 0.6$$

$$\Delta D' = 1.25 \times (P0 - P1) + 0.5$$

One finally obtains:

$$D2 = D1 + 0.3 P_{preset} + 1.25 \ P0 - 1.583 \ P1 - 0.1$$

The insufflation pressure, measured downstream of the pneumatic assembly as indicated above is preferably voluntarily limited to a maximum threshold in order to reduce the risks of cardio-vascular accidents for the patient. In order to take into account the dynamic component of the insufflation pressure this threshold, also called the safety pressure, is modulated as a function of the flow. According to a particular embodiment the safety pressure is modulated by an increasing linear flow function to a particular flow value and above this flow value the safety pressure is constant so as to set an absolute top limit to the insufflation pressure. The diagram of FIG. 4 illustrates by way of example such a variation rule for the security pressure.

In order to take into account modifications that can occur at any instant in the configuration of the insufflation path (kinking of the insufflation tube, displacement of the insufflation needle, etc.) the apparatus operates; cyclically (cycles of 2 to 3 seconds for example), all the parameters such as defined above being recalculated for each cycle. After each rest phase the apparatus restarts at minimal output.

When during a cycle of progressions of flows, the insufflation pressure exceeds the safety pressure discussed above, the insufflation is stopped instantly and the apparatus reduces the gas flow according to the rule illustrated by FIG. 4.

The insufflator stops when the calculated intracavity pressure is equal to the preset pressure. FIG. 5 is a diagram of pressure during a cycle with increasing gas flows, illustrating the successive insufflation times with their distinct flow rates until the preset pressure is reached, the insufflation being stopped at an intermediate instant when the security pressure $P_{max}$ is reached.

BRIEF DESCRIPTION OF THE DRAWING

The invention will be better understood with the help of the description that follows, with reference to the annexed schematic drawing showing by way of nonlimiting example an embodiment of this medical insufflator with automatic control of the gas flow.

SPECIFIC DESCRIPTION

Figure 1:
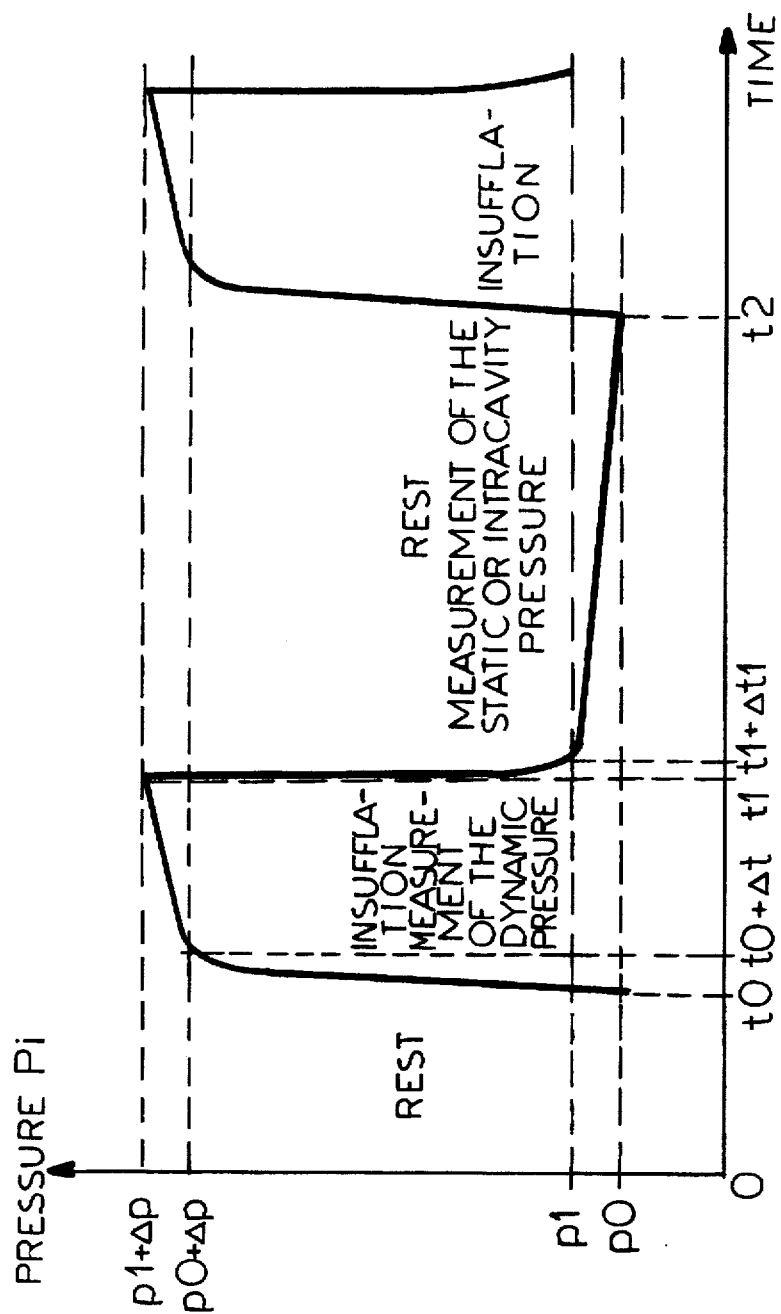
FIGS. 1 through 5 are graphs illustrating the present invention as described above.
Figure 2:
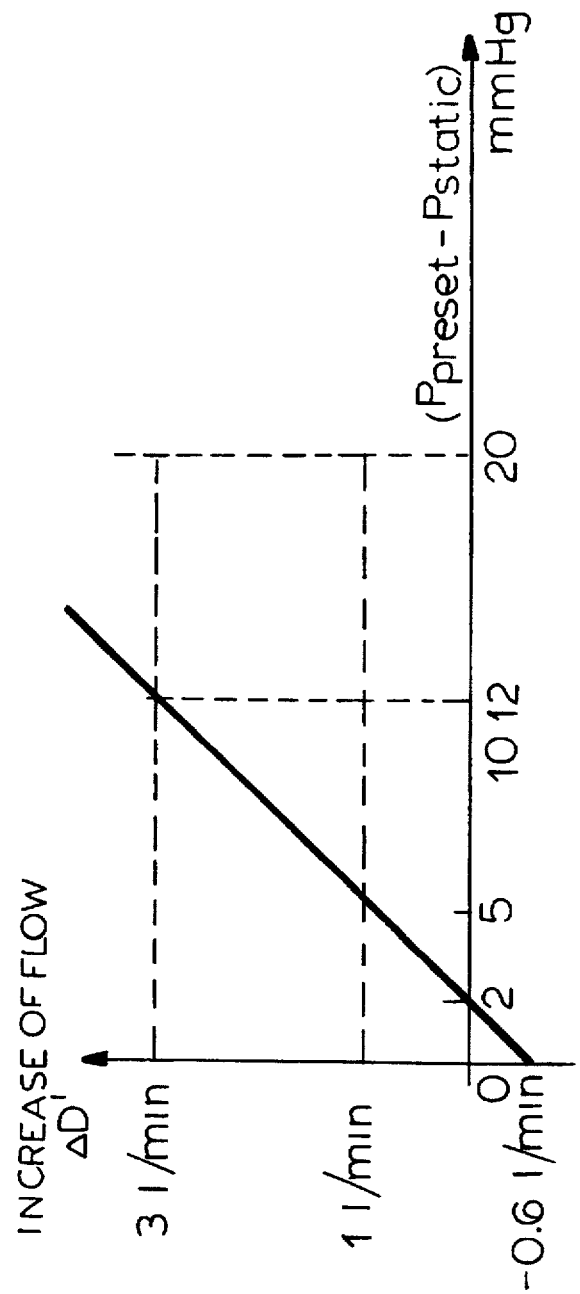
Figure 3:
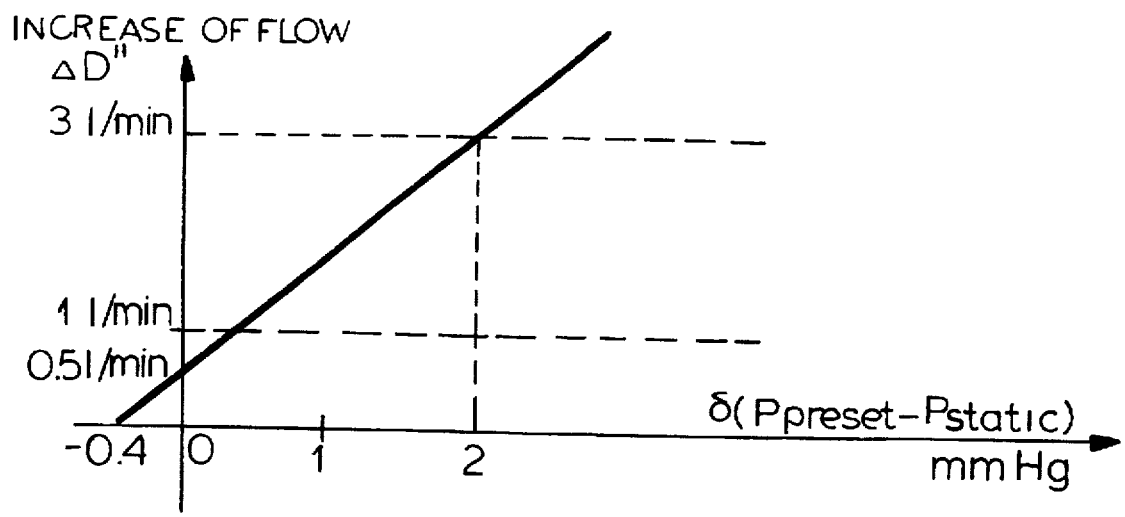
Figure 4:
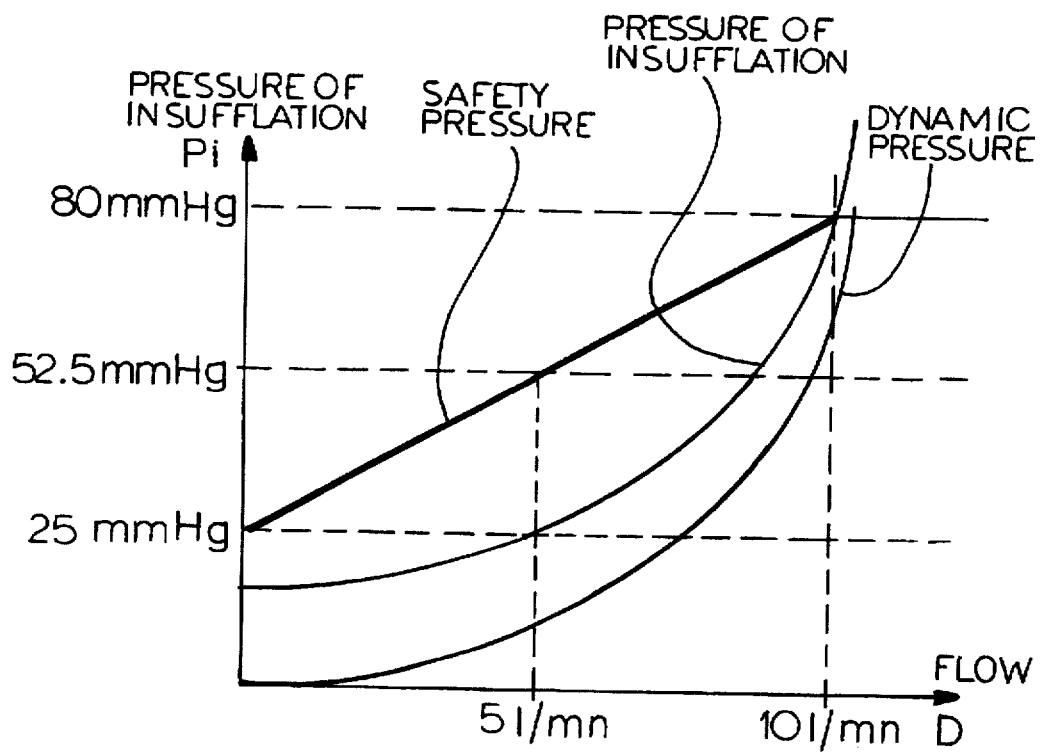
Figure 5:
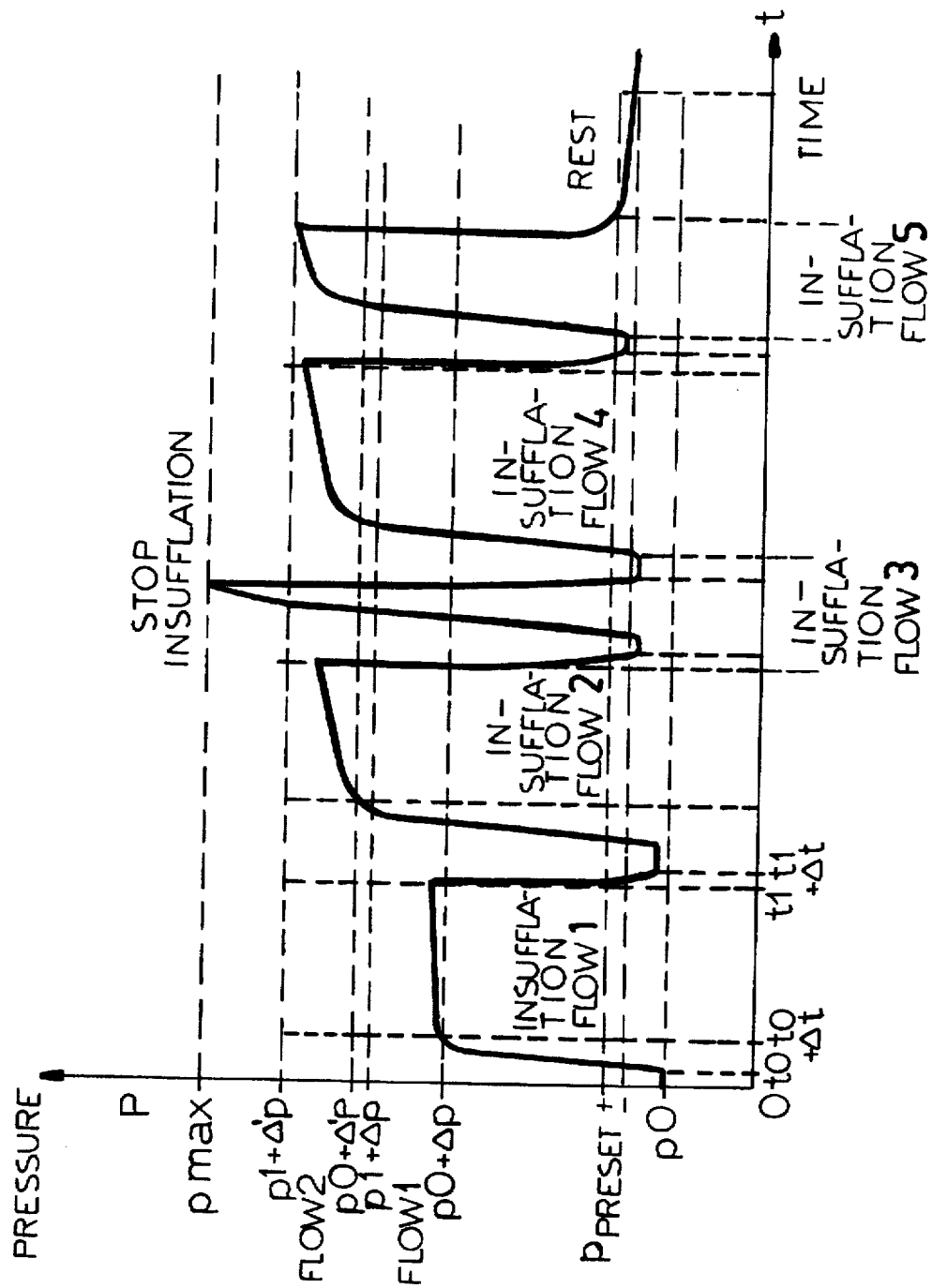
Figure 6:
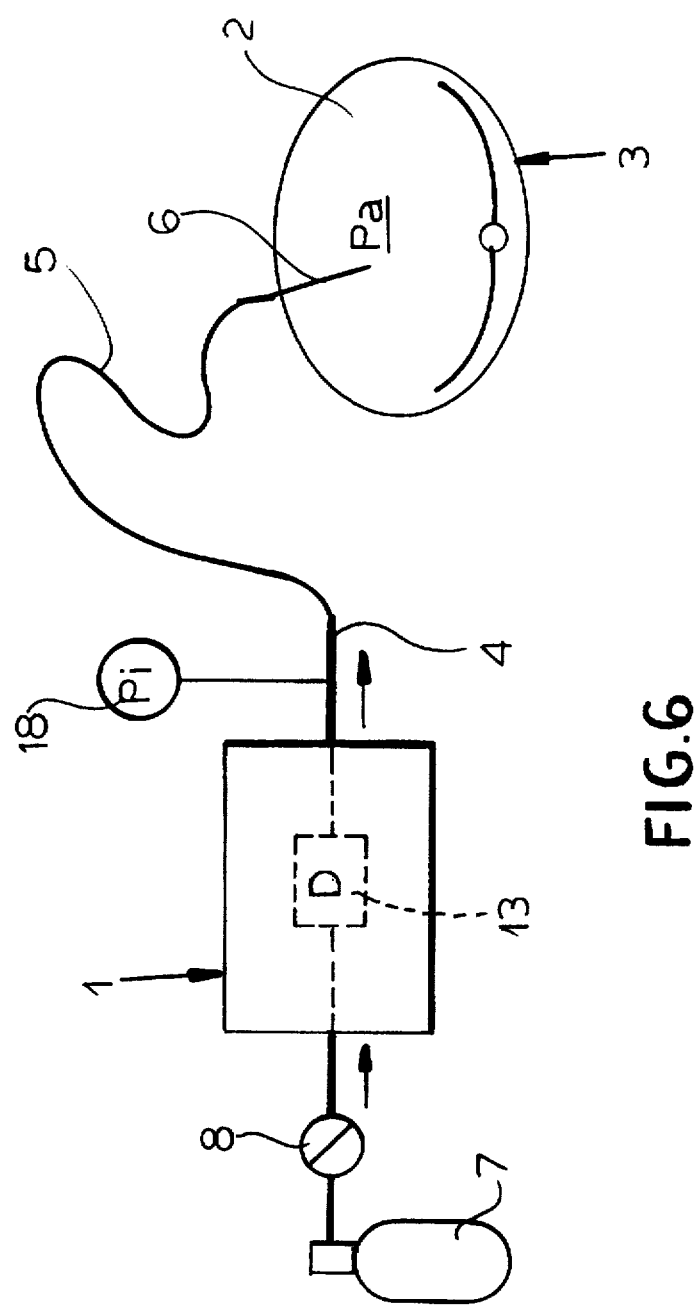
FIG. 6 is a basic diagram showing the medical insufflator and its environment.

The medical insufflator shown generally at reference 1 in FIG. 6 ensures the insufflation of a neutral gas, such as carbon dioxide, $CO_2$, into a surgical cavity 2 of a patient 3. The insufflation of gas into the surgical cavity 2 is done from the apparatus through the intermediary of a flow path having a gas outlet 4, a flexible connecting tube 5, and a Veress needle 6.

The gas is held in reserve as a liquid at high pressure (for example 49 bar) in a bottle 7 whose outlet is provided with a primary expander 8 that drops the gas pressure to a lower pressure that is constant and accurately controlled, for example 3 bar.

Figure 7:
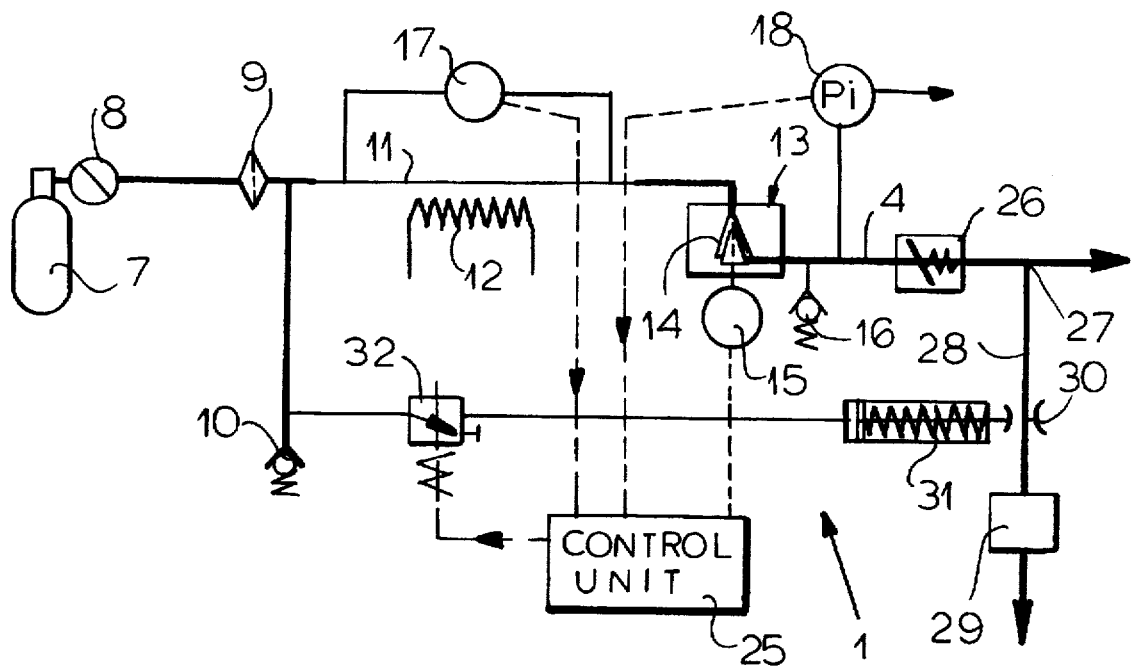
FIG. 7 is a synoptic diagram of the medical insufflator according to the present invention.

Inside the housing of the apparatus 1 as shown in FIG. 7 there is a secondary expander stage comprised going from upstream to downstream of:

a filter 9, for example of a porosity of 5 μm an input safety valve 10 set for example at a pressure of 3.5 bar, an expanding capillary tube 11 maintained at a constant temperature by a heater 12 and set up for laminar flow, a motorized flow-control valve 13 of the proportional type having a nozzle 14 operated by a motor 15 under electronic control, an output safety valve 16 set for example at a pressure of 0.2 bar, the outlet 4 to the gas insufflation flow path into the surgical cavity 2.

A differential pressure sensor 17 is connected to the expanding capillary tube. Another pressure sensor 18 at the outlet 4 to the insufflation flow path (see also FIG. 6) directly measures the insufflation pressure Pi. The intracavity pressure Pa is calculated from the detected insufflation pressure P1 and from an evaluation of the loss of pressure in the insufflation path.

Figure 8:
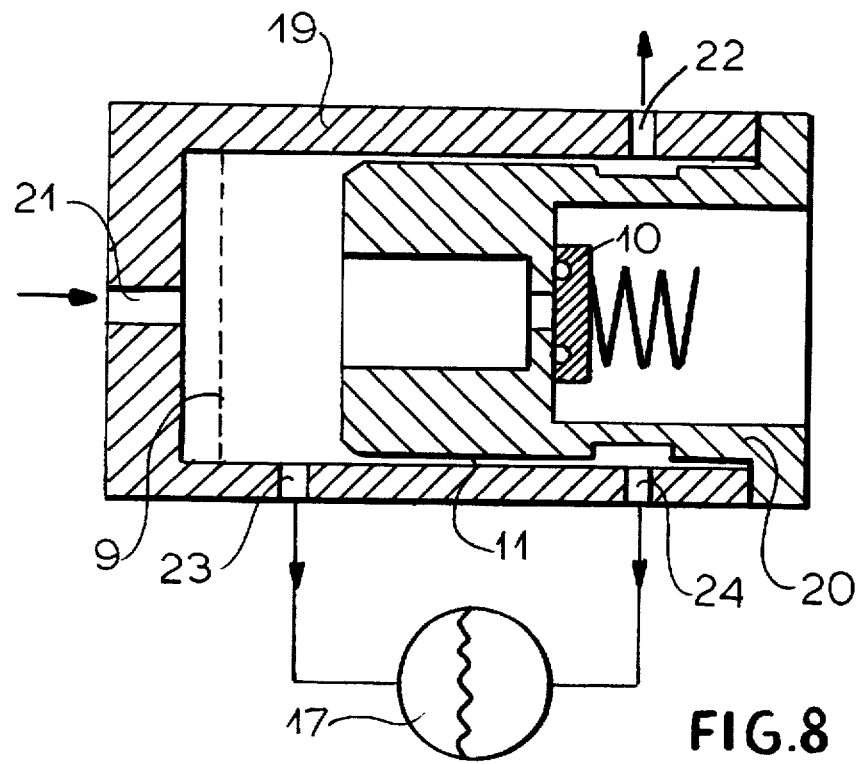
FIG. 8 is a detail sectional view of a embodiment of the capillary conduit which is connected to the differential pressure sensor.

With reference to FIG. 8 an advantageous embodiment of the expansion capillary 11 is shown which is embodied from two cylindrical elements 19 and 20, one mounted coaxially inside the other. The first cylindrical element 19, the outside element, has a gas-intake port 21 at one end and contains the filter 9. The second cylindrical element 20, the inside element, has at its center the input safety valve 10. Between the two cylindrical elements 19 and 20 there is an annular space whose thickness (measured radially) is for example 0.16 mm and which forms the capillary conduit 11. The gas output takes place laterally at 22 through an orifice bored through the wall of the first cylindrical element 19 downstream of the annular-section capillary conduit 11.

The differential-pressure sensor 17 uses a first lateral pressure tap 23 constituted as an orifice bored in the wall of the first cylindrical element 19 upstream of the annular-section capillary conduit 11 and a second lateral pressure tap 24 constituted as another orifice bored in the wall of the first cylindrical element 19 downstream of the capillary conduit 11.

The two pressure sensors 17 and 18 are connected to an electronic measuring and control unit 25 which operates the flow-control valve 13 according to the monitoring procedures described above, mainly to maintain the intracavity pressure Pa at the preset level while limiting the insufflation pressure Pi to the desired threshold safety level.

A check valve 26 at the outlet of the insufflation flow path prevents any pollution of the apparatus from liquid or vapors coming back up whereas the compensation for overpressures by aspiration on the same connecting tube 5 as that one intended for the insufflation of the gas into the surgical cavity 2 is itself a sure cause of pollution. This check valves 26 is mounted on a Y-joint 27 mounted at the upstream end of the connecting tube 5 and from which extends a branch tube 28 with smoke filter 29 that allows overpressures to escape to the exterior while preventing the emission of noxious vapors (laser for example) into the air of the operating room. A valve device 30, such as a system for pinching shut the tube, is operated by a small pneumatic cylinder 31 and allows one to control the aspiration and the escape through the tube 28. To guarantee the sterility of this assembly the tubes 5 and 28 and the vapor filter 29 are preferably of the single-use type.

The pneumatic cylinder 31 of the system for crushing or pinching the tube 30 can either be controlled automatically when an overpressure is detected through the intermediary of an escape solenoid valve 32 operated by the calculated intracavity pressure or manually in order to allow the evacuation of vapors. When the system 30 is open no pressure measurements are taken because the sensor 18 can only measure the escape pressure which is near the ambient pressure. This device should only work for overpressures of some duration; its automatic mode is thus on the one hand to some extent time dependent so as not to respond to certain sporadic effects due for example to the introduction of instruments by the surgeon and on the other hand limited. to intracavity pressure equal or greater than the preset pressure increased by a predetermined amount.

Whereas the operation described up to now relates to the normal insufflation process, it is advisable to add that the apparatus according to the invention also allows one to execute a particular cycle for monitoring the proper implantation of the needle before insufflation. To this end it is to be remembered that the practitioners of endoscope normally inject before insufflation a small amount of air (about 20 cm$^3$) by means of a syringe through the insufflation needle to be sure that it is not inserted into a blood vessel or between the layers of the peritoneum. The intraabdominal pressure is normally a little less than the ambient atmospheric pressure so that the injection of 20 cm$^3$ of air into a cavity of more than 10 dm$^3$ does not create any significant change of the intraabdominal pressure; this effect is achieved by the absorption of the gas by the overall peritoneal surface. If the needle has not reached to the abdominal cavity, if it is inserted between two peritoneal layers or adherents or is stuck into a loop of intestine, the injection of 20 cm$^3$ of air will cause a variation of the gas pressure inside the cavity where the injection takes place and the piston of the syringe will allow a certain "elastic" reaspiration. Thanks to the apparatus of the present invention this manual test is replaced by a test enabling or disabling operation of the insufflator. A particular command from the apparatus automatically starts the injection of predetermined small quantity, for example 20 cm$^3$ of gas at the minimal flow rate of 1 l/min. The static (intraabdominal) pressure is measured before the injection. A second measurement is taken after this injection. If the two measurements differ by more than a certain tolerance threshold amount, the apparatus is put on hold and an alarm signal is emitted.

Finally it is to be noted that the heater 12, which can be an electrical-resistance heater, not only allows one to maintain the gas at a constant temperature in the capillary 11 for the measurement of the gas flow via the differential pressure sensor 17 but also ensures the reheating of this gas (cooled by the expansion) to a temperature compatible with that of the body, that is between 35° C. and 40° C. and preferably between 38° C. an 40° C. before insufflation into the abdominal or other surgical cavity.

I claim:

1. A method of operating a medical insufflator comprising:

a flexible tube having a downstream end provided with a needle and an upstream end, the tube and needle forming an insufflation flow path for a neutral gas into a surgical cavity into which the needle is inserted, a supply of the neutral gas under pressure connected to the upstream end, and a flow-control valve along the flow path at the upstream end, the method comprising the steps of:

measuring an insufflation pressure at the upstream end of the insufflation path, continuously calculating intracavity pressure from the insufflation pressure by evaluating loss of pressure of the flow path, comparing the calculated inntracavity pressure and a preset value of this intracavity pressure, controlling the flow-control valve as a function of the result of the comparison with the above-mentioned preset value in order to continuously supply a flow the neutral gas that is minimally sufficient to compensate for leakage of gas from the surgical cavity and to maintain the intracavity pressure generally equal to the preset value; and compensating for leaks from surgical cavity by evaluating the derivative with respect to time of the offset between the preset pressure value and the intracavity pressure.

2. The method defined in claim 1 further comprising the steps in each of a succession of cycles of sequentially measuring the intracavity pressure at a first instant prior to insufflation when the intracavity pressure is equal to the static pressure at the upstream end of the insufflation flow path, displaying the measured intracavity pressure, starting insufflation at the first instant with a flow that stays constant during the current cycle, measuring the insufflation pressure at a second instant after the first instant, calculating the loss of pressure of the flow path as the difference between the pressures measured at the first and second instants, recording to memory the measured loss of pressure specific to the current cycle, measuring the dynamic insufflation pressure at a third instant after the second instant, measuring the intracavity pressure at the third instant, and displaying the intracavity pressure determined at the third instant and comparing it with the preset value.

3. The method defined in claim 1, further comprising means for defining and changing a threshold of the insufflation pressure according to a linear function derived from the gas flow while maintaining this threshold at a constant level for flows above a particular flow level, insufflation being stopped in a cycle of progression of flows when the insufflation pressure exceeds said safety pressure.

4. The method defined in claim 1 wherein a downstream end of the flow path is provided with a check valve which is connected in a Y-joint from which extends a branch tube provided with a vapor filter for venting intracavity overpressures to the outside, and with a valve-type device for ensuring monitoring of the aspiration and escape via the tube either automatically or manually, no pressure measurements being done when this device is open.

5. A method of operating a medical insufflator comprising:
- a flexible tube having a downstream end providing with need and an upstream end, the tube and needle forming an insufflation flow path for a neutral gas into a surgical cavity into which the needle is inserted,
- a supply of neutral gas under pressure connected to the upstream end, and
- a pneumatic control assembly comprised of the following in order from the gas supply to the downstream end:
  - primary expansion means for reducing to a low accurate pressure the pressure of the gas to be insufflated at the output of the supply of gas,
  - a filter,
  - an input safety valve,
  - a secondary expanding capillary creating laminar flow and to which is associated a differential pressure sensor that determines the instantaneous flow at the neutral gas,
  - a proportional flow-control valve that is opened electrically in accordance with the instantaneous flow and the flow,
  - an output safety valve, and
  - a gas outlet associated with measuring means for the insufflation pressure used for calculating and controlling (the) an intracavity pressure, the method comprising the steps of:
- measuring an insufflation pressure at the upstream end of the insufflation path,
- continuously calculating intracavity pressure from the insufflation pressure by evaluating loss of pressure of the flow path,
- comparing the calculated intracavity pressure and a preset value of this intracavity pressure,
- controlling the flow-control valve as a function of the result of the comparison with the above-mentioned preset value in order to continuously supply a flow of the neutral gas that is minimally sufficient to compensate for leakage of the surgical cavity and to maintain the intracavity pressure generally equal to the preset value.

6. The method defined in claim 5 wherein the pneumatic control assembly also has means for maintaining temperature by reheating the gas flowing through the capillary.

7. The method defined in claim 6 wherein the expanding capillary and the differential pressure sensor are formed from two coaxial cylindrical element, one mounted in the other, the capillary being formed by an annular-section space between the two cylindrical elements while two pressure taps are in the outside cylindrical element, respectively upstream and downstream from the region forming the capillary and serve to supply the differential pressure sensor that determines the instantaneous gas flow.

8. The method defined in claim 7 wherein the input safety valve is connected to the expansion capillary at a center of the inside cylindrical element.

* * * * *